United States Patent [19]
Efron et al.

[11] Patent Number: 5,081,542
[45] Date of Patent: Jan. 14, 1992

[54] LIQUID CRYSTAL LIGHT VALVE GOGGLES FOR EYE PROTECTION

[75] Inventors: Uzi Efron, Los Angeles; Shin-Tson Wu, Northridge, both of Calif.; Tsung-Yuan Hsu, Westlake Village, Calif.; Wayne Schoenmakers, Winnetka, Ill.

[73] Assignee: Hughes Aircraft Company, Los Angeles, Calif.

[21] Appl. No.: 450,118

[22] Filed: Dec. 12, 1989

[51] Int. Cl.⁵ ........................ G02F 1/133; G09G 3/02
[52] U.S. Cl. ........................................ 359/41; 359/42; 359/44; 359/67; 359/72; 340/705
[58] Field of Search .................. 350/331 R, 338, 342; 2/426; 340/705

[56] References Cited

U.S. PATENT DOCUMENTS

| | | | |
|---|---|---|---|
| 4,424,529 | 1/1984 | Roese et al. | 358/88 |
| 4,462,661 | 7/1984 | Witt | 350/331 R |
| 4,561,731 | 12/1985 | Kley | 350/331 R |
| 4,997,263 | 3/1991 | Cohen et al. | 350/331 R |

OTHER PUBLICATIONS

Moran, "Integrated Military Aircraft Displays and Controls," SID Digest, Apr. 1980, pp. 32-33.
"The Silicon Liquid-Crystal Light Valve", U. Efron et al., Journal of Applied Physics, vol. 57 (4), Feb. 15, 1985, pp. 1356-1368.

Primary Examiner—Stanley D. Miller
Assistant Examiner—Anita Pellman Gross
Attorney, Agent, or Firm—V. D. Duraiswamy; W. K. Denson-Low

[57] ABSTRACT

An eye protection device 10 comprising a liquid crystal light valve 20 for providing an image of a scene. The light valve images the field of view under observation in a spectral range which matches the human eye. It will automatically reject a laser threat by simply absorbing the energy therefrom in the photoconductive layer thereof. Thus, the invention 10 provides a broad spectrum, zero response time, angle and polarization independent, sensitive eye protection device having a fast recovery time, high extinction coefficient and a high damage threshold. Hence, the invention is expected to be of significant utility to personnel operating in hostile environments.

29 Claims, 4 Drawing Sheets

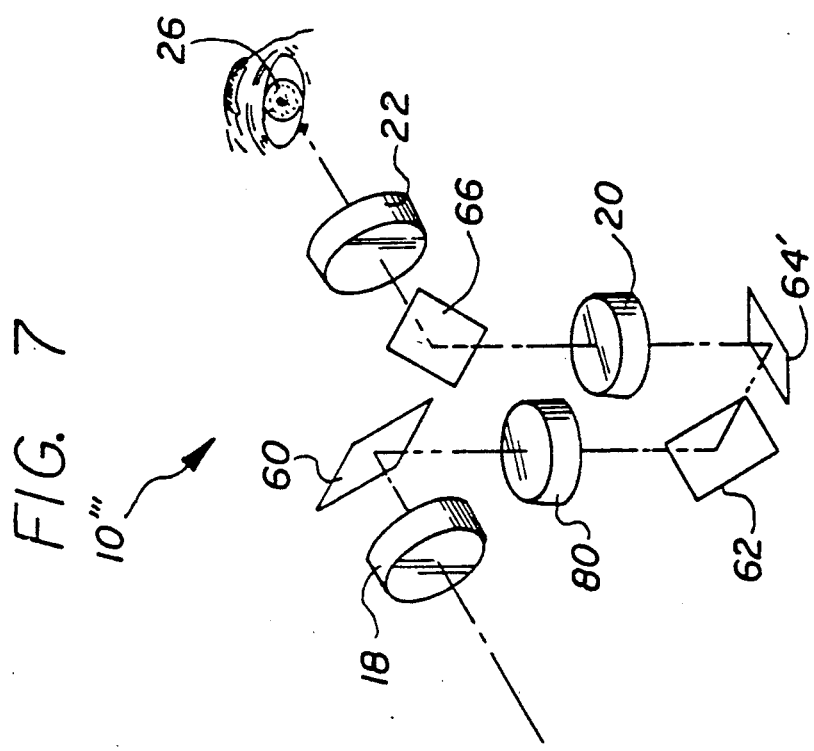
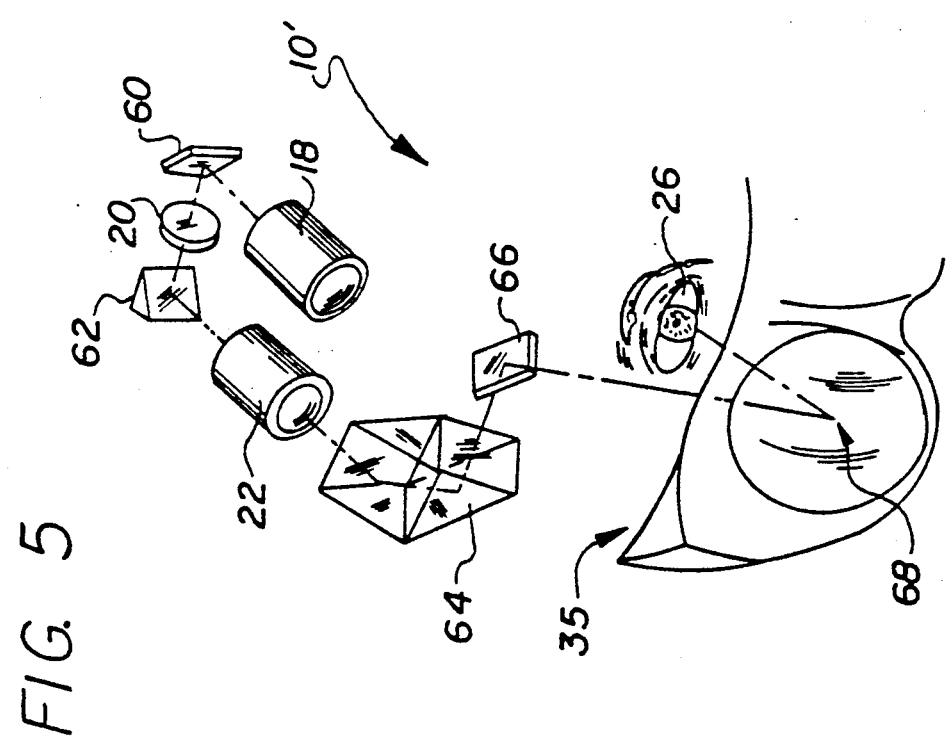

LIQUID CRYSTAL LIGHT VALVE GOGGLES FOR EYE PROTECTION

This invention was made in performance of work under the Department of the Navy Contract No. N62269-87-C-0263. The Government of the United States of America therefore has certain rights in this invention.

BACKGROUND OF THE INVENTION

1. Field of the Invention

The present invention relates to eye protection devices. More specifically, the present invention relates to techniques for preventing eye damage due to high intensity laser radiation.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

2. Description of the Related Art

The threat of the use of laser radiation to induce vision impairment has prompted a concern for the ocular welfare of personnel operating in hostile environments. This has lead to the recognition of certain requirements to insure adequate eye protection against such threats. Generally, the eye protection gear should have a broad spectrum to block incident radiation over a wide bandwidth. The eye protection device should have a zero response time to insure that the device will react quickly enough to protect the eye from short pulses of intense radiation. It should operate independent the angle and polarization of the incident radiation. It should be sensitive to energy in the visible to near infrared range. The device should have a fast recovery time and a high damage threshold.

Conventional eye protection technologies do not adequately meet these requirements. Multi-channel image intensifiers can be used as efficient image converters for eye protection. These devices utilize photosensitive materials which generate electrons. The electrons are amplified and bombarded on a phosphorous screen to create an image of a scene.

Unfortunately, the photo-cathode of image converters are typically susceptible to breakdown in response to an intense laser pulse. The recovery time from such breakdown is too slow for many current applications. And these devices tend to be complicated often requiring high voltages. This class of devices also includes electrochromic effect based goggles which tend to be too slow and have a extinction coefficient which is too low (viz., energy leakage too high) for the noted application.

Visors based on narrow band filters implemented with multiple optical thin film layers can only reject radiation at known wavelengths. No protection is provided against arbitrary radiation in the broad visible spectrum such as that resulting from a dye laser.

Nonlinear optical materials in the desired region remain as an unproven concept. No optical material is known which features sufficiently high sensitivity and response time to meet the demanding requirements of eye protection. In addition, the leakage of any such devices would probably be too high.

Thus, there is a need in the art for a broad spectrum, zero response time angle and polarization independent, sensitive eye protection device having a fast recovery time, high extinction coefficient and a high damage threshold.

SUMMARY OF THE INVENTION

The need in the art is addressed by the eye protection device of the present invention which comprises a liquid crystal light valve for providing an image of a scene. The light valve images the field of view under observation in a spectral range which matches the human eye. It will automatically reject a laser threat by simply absorbing the energy therefrom in the photoconductive layer thereof. Thus, the invention provides a broad spectrum, zero response time, angle and polarization independent, sensitive eye protection device having a fast recovery time, high extinction coefficient and a high damage threshold. Hence, the invention is expected to be of significant utility to personnel operating in hostile environments.

BRIEF DESCRIPTION OF THE DRAWINGS

FIG. 5 is a first alternative embodiment of the eye protection device of the present invention.

FIG. 7 is a third alternative embodiment of the eye protection device of the present invention.

DESCRIPTION OF THE INVENTION

Illustrative embodiments and exemplary applications will now be described with reference to the accompanying drawings to disclose the advantageous teachings of the present invention.

Figure 1:
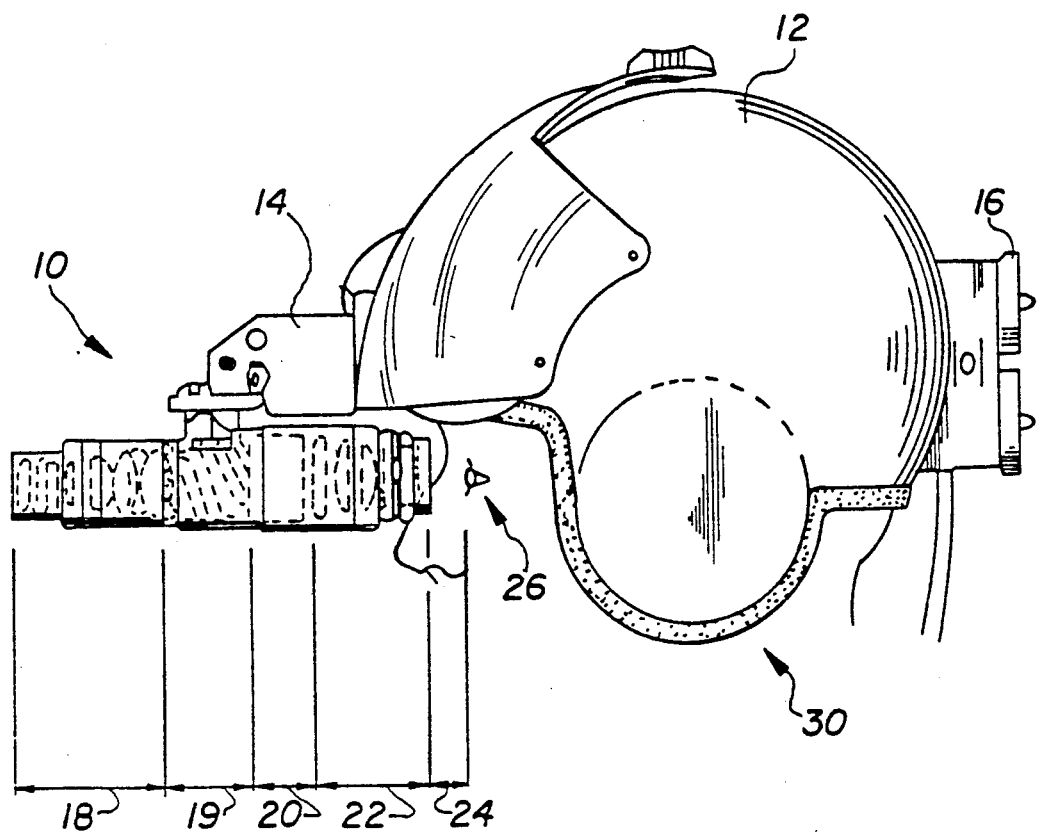
FIG. 1 is a side view of the eye protection goggles of the present invention mounted on a helmet of conventional design.

FIG. 1 is a side view of the eye protection goggles 10 of the present invention mounted on a helmet 12 of conventional design. The goggles 10 are pivotally attached to the helmet 12 by a modified Anvis bracket 14. Counter weights 16 mounted on the rear of the helmet 12 counteract the weight of the goggles 10 on the front of the helmet 12. As shown in phantom in FIG. 1, the goggles 10 include an objective lens 18, a twisting optical fiber 19, a silicon liquid crystal light valve (LCLV) 20, and an eyepiece lens 22. The distance 24 represents the eye relief between the eyepiece lens 22 and the eye 26 of the observer 30.

Figure 2:
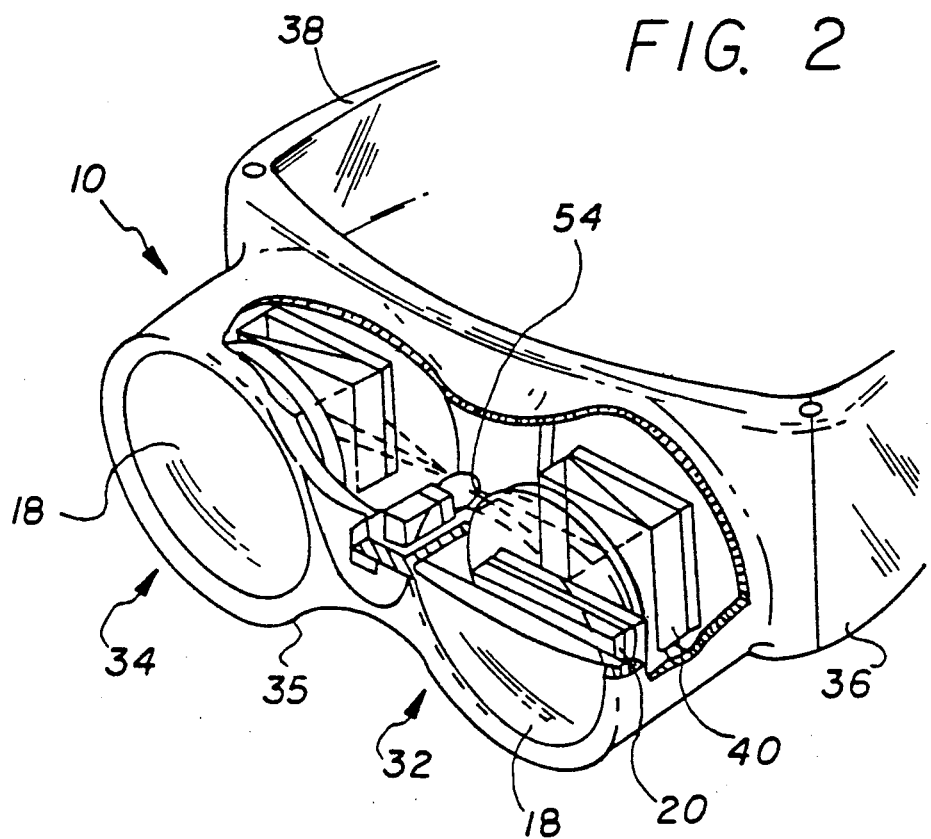
FIG. 2 is a perspective view, partially in section, of an illustrative implementation of the liquid crystal light valve (LCLV) of the present invention.

FIG. 2 is a perspective view, partially in section, of an illustrative implementation of the liquid crystal light valve 10 of the present invention. The left and right goggles 32 and 34 are encased within a frame 35 constructed of plastic or other suitable material. The embodiment of FIG. 2 shows first and second straps 36 and 38 for retaining the goggles 32 and 34 in a proper viewing position. A green LED 54 is used as a readout light source.

Figure 3:
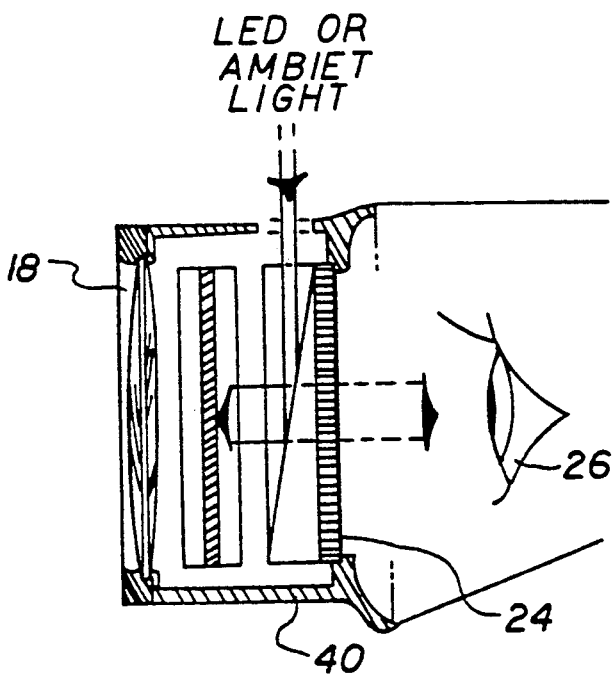
(FIG. 3 is a sectional side view of a single goggle of the illustrative implementation of FIG. 2.

FIG. 3 is a sectional side view of a single goggle of the illustrative implementation of FIG. 2. As shown more clearly in FIG. 3, each goggle 32 and 34 includes the objective lens 18, the liquid crystal light valve 20, a polarizing beam splitter 40 and the eye piece lens 24.

Figure 4:
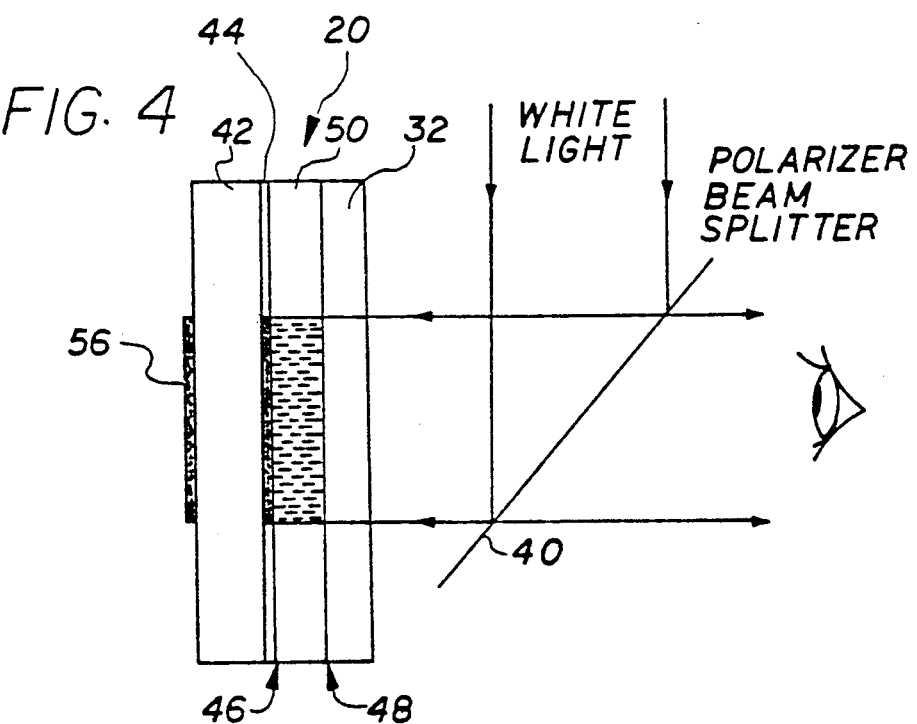
FIG. 4 is a schematic diagram of a silicon liquid crystal light valve.

As illustrated in FIG. 4, the light valve 20 is of a conventional reflective design including a silicon photoconductive layer 42, a dielectric mirror 44, a first conductive electrode layer 46 of indium-tin-oxide (ITO) or other suitable material, a liquid crystal layer 50, a second ITO layer 48, and a glass layer 52. The design and construction of liquid crystal light valve 20 is known in the art, see for example "The Silicon Liquid-Crystal Light Valve", by U. Efron et al., in *Journal of Applied Physics*. vol. 57, no. 4, pp. 1356-1368, Feb. 15, 1985.

A single crystalline silicon LCLV was chosen for the following reasons:

1) the spectral range of the silicon photoconductor is extensive (0.4-1.12 μm);

2) the response time of the LCLV (typically 20 msec) is adequately fast for the human eye (approx. 100 msec.) response;

3) the resolution of the device at an aperture of 3-4 cm may exceed 1000 lines, which is the estimated required resolution for the human eye;

4) the room-temperature operation of the device is, of course, compatible with the temperature of the human body; and 5) the sensitivity of the Si-LCLV is equivalent to a dimly lit room, allowing operational range between full daylight and possibly a moonlit scene, (further sensitivity can be achieved by incorporating gain into the device using the avalanche principle, for example).

The use of a silicon photoconductor also allows imaging in the near infrared region (up to approx. 1.1 μm due to the large thickness of the silicon wafer. In order to block infrared and near infrared threats, a metal matrix mirror can be constructed using metal grid lines or the method of overhanging channel protection. In both methods, the pixels as well as the channel areas around the pixels will be covered by a reflective metal (e.g. aluminum) and will therefore block any infrared threat from reaching the eyes. For imaging mid-IR radiation, some leadsalts photoconductors, such as PbS, PbSe, PbTe and their alloys can be used.

In operation, the objective lens 18 focuses the input image onto the liquid crystal light valve 20. The photoconductive surface 42 of the light valve 20 receives the input energy and generates electron hole pairs which are driven by an applied electric field to cause a voltage drop on the liquid crystal layer. These spatially resolved voltages induce a phase change of the readout light thereby replicating the input image on the viewing side of the light valve 20. The silicon photoconductor 42 allows imaging in the 400-700 nm spectral region used by the human eye and will automatically absorb any excessive high intensity radiation. If, however, the input light intensity is outside the dynamic range of the light valve, i.e., one to several hundred microwatts per square centimeter, the output image will be slightly blurred. The degree of image blurring is proportional to the incident light intensity. As the incident laser pulse exceeds approx. $10^7 W/cm^2$, a local damage on the silicon will appear. The readout light intensity (approx. $100\mu W/cm^2$) is controlled by the current of the LED used which can be powered by a 9-volt battery or by a solar cell. Thus, a high intensity beam of a potentially blinding level of say >50 watts/cm², could be reduced by over five orders of magnitude to a safe brightness level incident on the observer's eyes. The LCLV goggles can also be incorporated with a head-up display to serve as a threat locator, range finder or target designator.

Returning to FIG. 2, a light emitting diode (LED) 54 is mounted within the frame 35 of the device 10 between the left and right goggles 32 and 34. As illustrated in FIGS. 3 and 4, light from the LED may be injected onto the viewing surface of the light valve at the glass 52 by the polarizing beam splitter 40 to facilitate readout. In order to cut down on power consumption, ambient light may be utilized during daytime by opening windows (e.g. at the upper part of the goggles) to replace the LED operation. The LED would be used when the ambient light is at a low level.

FIG. 4 shows a color filter 56 for making a color display from the use of white light illumination. The color filters are deposited on each pixel in the photoconductor and dielectric mirror sides.

In order to allow operation of the LCLV under cold weather conditions, heating electrodes (not shown) could be used combined with proper thermal insulation of the LCLV structures. If adequately insulated from the surroundings, it may be possible to rely on body temperature to supply the necessary heat for maintaining the temperature of the LCLV.

In order to reduce the length of the goggles, a holographic lens may be fabricated on the output window of the beam splitter 40.

The twisting optical fibers 19 (shown in phantom in FIG. 1) serve to invert the image on the light valve for an upright presentation to the viewer. FIG. 5 shows an alternative technique for reorienting the image. In this embodiment 10', the LCLV 20 is situated between two folding mirrors 60 and 62. The output image is directed through the eyepiece lens 22 to a mirrored glass prism 64. The prism 64 inverts the image and passes it to the eye 26 via a folding mirror 66 and a holographic reflector 68 inside the lens of the goggle 35.

Figure 6:
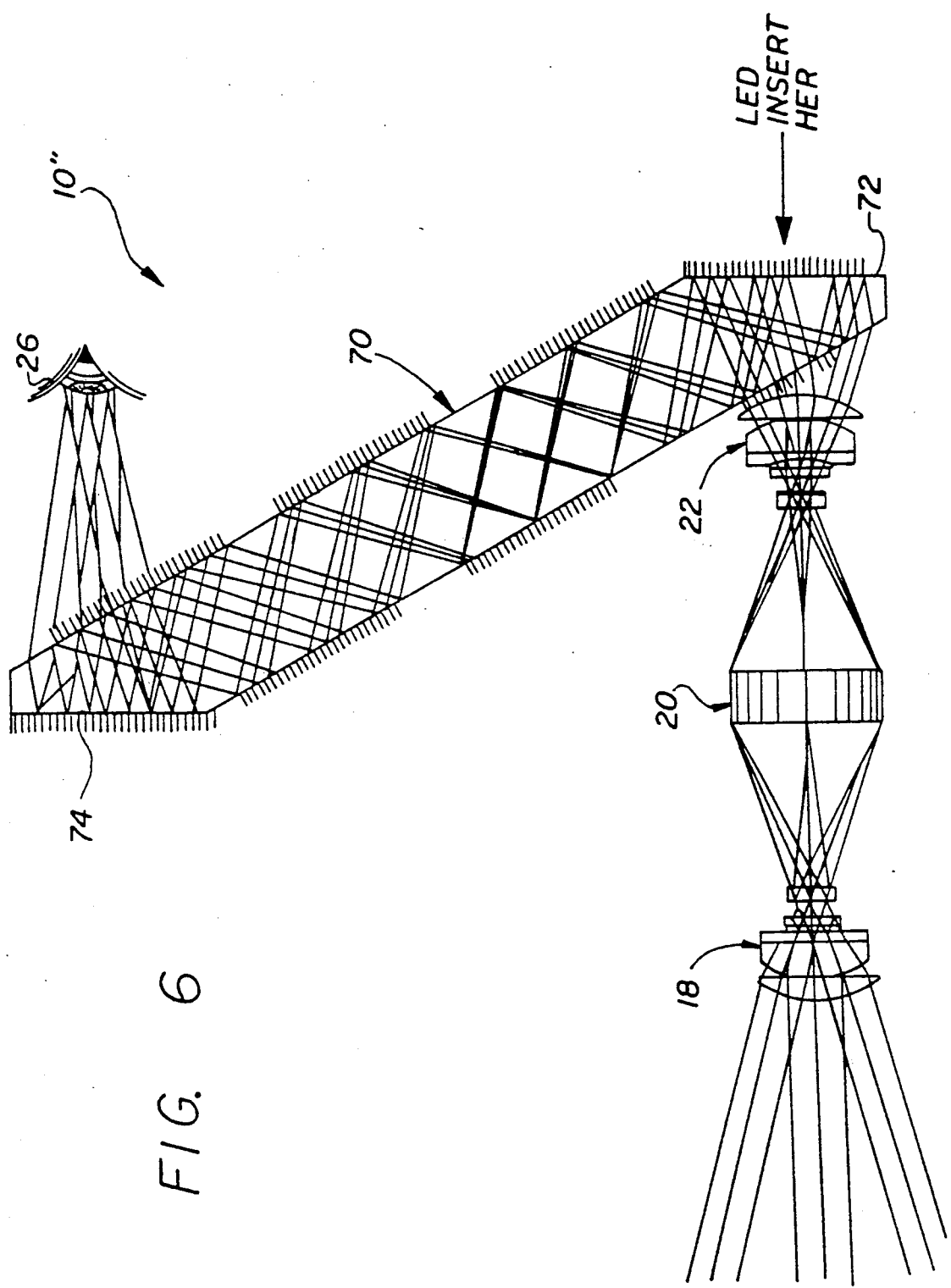
FIG. 6 is a second alternative embodiment of the eye protection device of the present invention.

The second alternative embodiment of FIG. 6 shows the use of an arm 70 constructed of reflective acrylic relay material. The arm 70 is movable into and out of the line of sight of the eye 26. The arm 70 includes two aluminized reflective surfaces 72 and 74. Optical ray traces are shown for the purpose of illustration.

FIG. 7 is a third alternative embodiment 10''' of the eye protection device of the present invention. In this embodiment, a relay lens 80 is situated between two of four folding mirrors 60, 62, 64 and 66 to bend the optical axis downward or upward thereby shortening the length of the goggles while simultaneously inverting the image.

Thus, the present invention has been described herein with reference to a particular embodiment for a particular application. Those having ordinary skill in the art and access to the present teachings will recognize additional modifications applications and embodiments within the scope thereof. For example, the invention is not limited to the optical arrangements illustrated herein.

It is therefore intended by the appended claims to cover any and all such applications, modifications and embodiments within the scope of the present invention.

Accordingly, What is claimed is:

1. An eye protection device comprising:
 a liquid crystal light valve for providing an image of
  a scene in a spectral range suitable for human viewing and for preventing harmful radiation from being transmitted for viewing, wherein said liquid crystal light valve includes a photoconductive layer, and means for supporting the light valve to facilitate the viewing thereof.

2. The invention of claim 1 wherein said photoconductive layer comprises silicon.

3. The invention of claim 2 wherein the silicon is single crystalline silicon.

4. The invention of claim 1 wherein the photoconductive layer comprises lead salts.

5. The invention of claim 1 including an objective lens mounted along the optical train of said light valve.

6. The invention of claim 5 including an eyepiece lens mounted along the optical axis of said light valve.

7. The invention of claim 1 including light emitting diode means for reading said light valve.

8. The invention of claim 1 including reflector means for reflecting said image to the eye of a viewer.

9. An eye protection device comprising:
a liquid crystal light valve for providing an image of a scene;
means for supporting the light valve to facilitate the viewing thereof;
reflector means for reflecting said image to the eye of a viewer; and
means for moving said reflecting means from a first position to a second position.

10. An eye protection device comprising:
a liquid crystal light valve for providing an image of a scene;
means for supporting the light valve to facilitate the viewing thereof;
reflector means for reflecting said image to the eye of a viewer; and
folding mirror means for folding the optical train of said device.

11. The invention of claim 10 including relay lens disposed in the optical train of said light valve.

12. An eye protection device comprising:
a liquid crystal light valve for providing an image of a scene;
means for supporting the light valve to facilitate the viewing thereof, and
means for inverting the image provided by said light valve.

13. The invention of claim 12 including twisting fiber mounted in the optical train of said light valve.

14. An eye protection device comprising:
a liquid crystal light valve for providing an image of a scene; and
means for supporting the light valve to facilitate the viewing thereof, wherein said means for supporting the light valve includes counter weights mounted on a helmet on which said device is installed.

15. Eye protection goggles comprising:
two reflective liquid crystal light valves for providing an image of a scene;
an objective lens for, one for each light valve, mounted along the optical train thereof;
an eyepiece lens, one for each light valve, mounted along the optical axis thereof; and
means for supporting the light valves to facilitate the viewing thereof.

16. The invention of claim 15 including light emitting diode means for reading said light valves.

17. The invention of claim 15 including reflector means for reflecting said image to the eye of a viewer.

18. The invention of claim 17 including means for moving said reflecting means from a first position to a second position.

19. The invention of claim 17 including folding mirror means for folding the optical train of said device.

20. The invention of claim 19 including relay lens disposed in the optical train of said light valves.

21. The invention of claim 15 including means for inverting the image provided by said light valves.

22. The invention of claim 21 including twisting fiber mounted in the optical train of said light valves.

23. The invention of claim 15 wherein said means for supporting the light valves includes counter weights mounted on a helmet on which said device is installed.

24. A target locator system comprising:
liquid crystal light valve goggles for imaging a scene in a spectral range suitable for human viewing, wherein said liquid crystal light valve includes a photoconductive layer, and
a head-up display.

25. An eye protection device comprising:
at least one liquid crystal light valve goggle for imaging a scene; and
a helmet to which said at least one liquid crystal light valve goggle is pivotally attached,
said liquid crystal light valve goggle including:
a photoconductive layer for receiving input images;
means on said photoconductive layer for blocking threat radiation, and
a layer comprising liquid crystal for modulating a readout light and replicating the input images for viewing in response to the input images received by said photoconductive layer.

26. The eye protection device of claim 25 further including:
a light emitting diode mounted for optical illumination of the viewing surface of said light valve.

27. The eye protection device of claim 25 wherein said liquid crystal light valve further includes heating electrodes.

28. The eye protection device of claim 25 wherein said goggle further includes a polarizing beam splitter having a holographic lens fabricated thereon.

29. The eye protection device of claim 25 wherein said means for blocking threat radiation includes:
metal matrix mirror having pixels and channels between said pixels, and
a reflective layer covering both said pixels and said channels.

* * * * *